US010111990B2

(12) United States Patent
Baxter et al.

(10) Patent No.: US 10,111,990 B2
(45) Date of Patent: Oct. 30, 2018

(54) CASSETTE CLAMP MECHANISM

(71) Applicant: Alcon Research, Ltd., Fort Worth, TX (US)

(72) Inventors: Vincent A. Baxter, Temecula, CA (US); Daniel J. Wilson, Lake Forest, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 0 days.

(21) Appl. No.: 15/459,807

(22) Filed: Mar. 15, 2017

(65) Prior Publication Data

US 2017/0181891 A1    Jun. 29, 2017

Related U.S. Application Data

(63) Continuation of application No. 14/076,418, filed on Nov. 11, 2013, now Pat. No. 9,713,660.

(60) Provisional application No. 61/740,530, filed on Dec. 21, 2012.

(51) Int. Cl.
| | | |
|---|---|---|
| *A61M 1/00* | (2006.01) | |
| *A61F 9/007* | (2006.01) | |
| *F04B 53/16* | (2006.01) | |

(52) U.S. Cl.
CPC ........ *A61M 1/0058* (2013.01); *A61F 9/00736* (2013.01); *A61F 9/00745* (2013.01); *A61M 2205/121* (2013.01); *A61M 2209/082* (2013.01); *A61M 2209/084* (2013.01); *A61M 2210/0612* (2013.01); *F04B 53/16* (2013.01)

(58) Field of Classification Search
CPC ........ A61M 2205/12; A61M 2205/121; A61M 2205/122; A61M 2205/123; A61M 2205/125; A61M 2205/126; A61M 2205/127; A61M 2205/128; A61M 1/00; A61M 1/0058; A61M 2210/0612; A61M 2209/082; A61M 2209/084; F04B 53/16; B65D 45/00; A61F 9/00736; A61F 9/00745

USPC ..... 417/360, 63, 477.2; 604/65, 294, 30, 34, 604/153; 292/44, 45, 54, 201, 256

See application file for complete search history.

(56) References Cited

U.S. PATENT DOCUMENTS

| | | | | |
|---|---|---|---|---|
| 4,758,220 | A * | 7/1988 | Sundblom | ........... A61F 9/00736 604/119 |
| 6,427,096 | B1 * | 7/2002 | Lewis | ............... H01L 21/67379 414/222.07 |
| 7,070,578 | B2 * | 7/2006 | Leukanech | ......... A61M 1/0058 292/201 |

(Continued)

*Primary Examiner* — Nathan C Zollinger

(57) ABSTRACT

A surgical cassette clamping system includes a mounting plate having a first side and a second side. A bracket system may be disposed adjacent the first side of the mounting plate. A clamp motor may be disposed adjacent the mounting plate and fixed relative to the mounting plate. The clamp motor may be operably connected to the bracket system to displace the bracket system relative to the mounting plate. The system may also include a plurality of pivot arms pivotably connected to the bracket system and extending adjacent the second side of the mounting plate. An engagement portion may be attached to each of the plurality of pivot arms that cooperatively engages the second side of the mounting plate, the engagement portion being operable to pivot the pivot arms when the bracket system moves relative to the mounting plate.

20 Claims, 11 Drawing Sheets

(56) References Cited

U.S. PATENT DOCUMENTS 9,713,660 B2 * 7/2017 Baxter ............... A61M 1/0058
2007/0286755 A1 * 12/2007 Williams ............ A61M 1/0058
417/477.2

* cited by examiner

CASSETTE CLAMP MECHANISM

PRIORITY CLAIM

This application:
(a) is a continuation application of U.S. patent application Ser. No. 14/076,418 titled "Cassette Clamp Mechanism" which was filed Nov. 11, 2013 whose inventors are Vincent A. Baxter and Daniel J. Wilson which is hereby incorporated by reference in its entirety as though fully and completely set forth herein, and
(b) claims the benefit of priority of U.S. Provisional Application Ser. No. 61/740,530 (U.S. patent application Ser. No. 14/076,418 claimed the benefit of priority of provisional application Ser. No. 61/740,530 titled "Cassette Clamp Mechanism" filed on Dec. 21, 2012, whose inventors are Vincent A. Baxter and Daniel J. Wilson), which is also hereby incorporated by reference in its entirety as though fully and completely set forth herein.

BACKGROUND

The devices, systems, and methods disclosed herein relate generally to cassette clamping mechanisms, and more particularly, to cassette clamping mechanisms used on surgical consoles.

Some surgical consoles receive single-use, replaceable elements, such as fluid cassettes. Accordingly, a new cassette may be associated with the console for each surgery performed. Since each surgical cassette is individually introduced onto the console, the alignment of the cassette on the console may deviate, albeit slightly, from cassette to cassette. In macro applications, this may not be noticeable, however, in some micro-surgical applications, these deviations can be undesirable. In order to provide precise and predictable control from cassette to cassette, particularly when small fluid flow differentials can impact the surgical environment, the cassette should be precisely located within the console with some degree of precision.

The present disclosure is directed to devices, systems, and methods that address one or more of the disadvantages of the prior art.

SUMMARY

In an exemplary aspect, the present disclosure is directed to a surgical cassette clamping system that includes a mounting plate having a first side and a second side. A bracket system may be disposed adjacent the first side of the mounting plate. The bracket system may include at least four connectors configured to engage the surgical cassette in a distributed manner to apply an evenly distributed clamping force on the surgical cassette. A clamp motor may be disposed adjacent the mounting plate and fixed relative to the mounting plate. The clamp motor may be operably connected to the bracket system to displace the bracket system relative to the mounting plate. The system may also include a plurality of pivot arms pivotably connected to the bracket system and extending adjacent the second side of the mounting plate. An engagement portion may be attached to each of the plurality of pivot arms that cooperatively engages the second side of the mounting plate, the engagement portion being operable to pivot the pivot arms when the bracket system moves relative to the mounting plate.

In an aspect, the bracket system comprises a first bracket and a second bracket each formed from sheet metal. In another aspect, the system includes a first sensor configured to detect the presence of the surgical cassette and includes a second sensor configured to monitor a position of a drive wheel driven by the clamp motor.

In an aspect, the system includes a spring extending between one of the plurality of pivot arms and the bracket system. The spring may connect to the bracket system at a first connecting location and may connect to the pivot arm at a second connecting location, the first connecting location and the second connecting location being located so that the spring force increases as the moment arm decreases to maintain a relatively consistent clamping force over a pivot range of about 10 degrees with the spring in continuous tension. In an aspect, a relatively consistent clamping force is a clamping force that deviates less than about 10% over the pivot range of about 10 degrees. In an aspect, the bracket system comprises a motion bracket and a clamp bracket, the clamp bracket comprising the fastening element and the motion bracket comprising the second connecting location.

In an aspect, the engagement portion is a roller configured to roll along a ramp on the mounting plate.

In another exemplary aspect, the present disclosure is directed to a surgical cassette clamping system including a bracket system comprising a fastening element configured to engage the surgical cassette; a pivot arm pivotably connected to the bracket system at a pivot location; and a spring extending between the pivot arm and the bracket system. The spring may connect to the bracket system at a first connecting location and connect to the pivot arm at a second connecting location, the first connecting location and the second connecting location being located so that the spring force increases as the moment arm decreases to maintain a relatively consistent clamping force over a pivot range of about 10 degrees with the spring in continuous tension.

In an aspect, the pivot arm comprises a roller spaced from the pivot location. In an aspect the system includes a ramp disposed relative to the roller, the ramp displacing the bracket system in a direction to clamp the surgical cassette with the fastening elements, the ramp forcing the pivot arm to pivot about the pivot location as the bracket system displaces.

In another exemplary aspect the present disclosure is directed to a method including receiving a surgical cassette on an orientation element configured to orient the surgical cassette for clamping in a surgical console; detecting the presence of the surgical cassette with a first sensor; engaging the surgical cassette with a plurality of fastening elements disposed adjacent corners of the surgical cassette to evenly distribute a clamping force and move the fastening elements in a first direction; and fixing the surgical cassette in place by moving the fastening elements in a second direction.

In an aspect, receiving a surgical cassette on an orientation element comprises receiving the surgical cassette on a plurality of projecting shelf pins shaped to correspond to features of the surgical cassette. In an aspect, engaging the surgical cassette further comprises engaging the surgical cassette with six fastening elements with a substantially equal clamping force on each fastening element. In an aspect, fixing the surgical cassette in place by moving the fastening elements in a second direction includes driving a bracket system along a ramp. In an aspect, the method includes maintaining the surgical cassette on the console with a plurality of retaining arms that engage a perimeter of the surgical cassette.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

The accompanying drawings illustrate embodiments of the devices and methods disclosed herein and together with the description, serve to explain the principles of the present disclosure.

DETAILED DESCRIPTION

Figure 1:
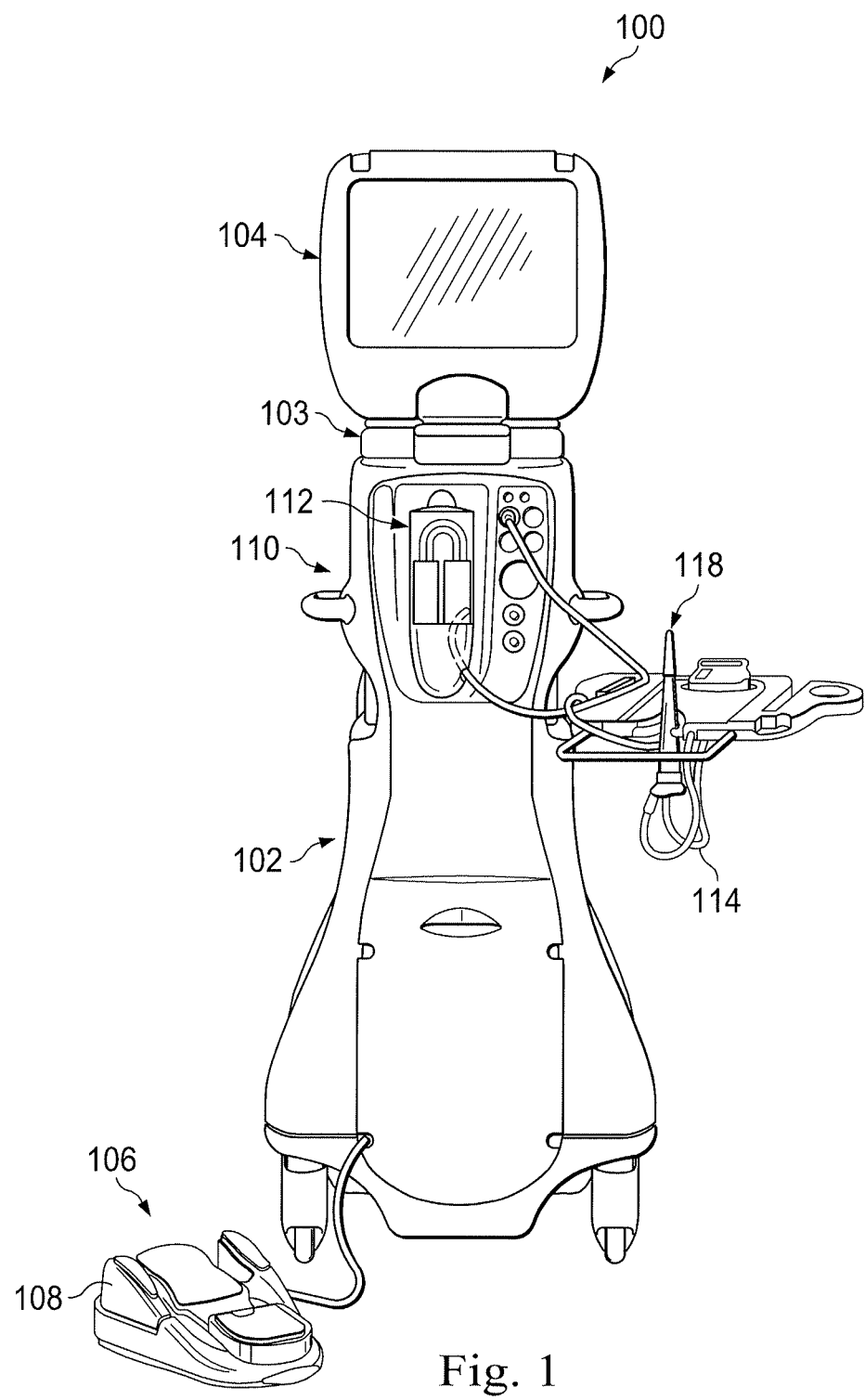
FIG. 1 illustrates a perspective view of an exemplary surgical console according to one embodiment consistent with the principles of the present disclosure.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described systems, devices, and methods, and any further application of the principles of the present disclosure are fully contemplated as would normally occur to one skilled in the art to which the disclosure relates. In particular, it is fully contemplated that the systems, devices, and/or methods described with respect to one embodiment may be combined with the features, components, and/or steps described with respect to other embodiments of the present disclosure. For the sake of brevity, however, the numerous iterations of these combinations will not be described separately. For simplicity, in some instances the same reference numbers are used throughout the drawings to refer to the same or like parts.

The devices, systems, and methods described herein consistently and securely attach a replaceable cassette with a surgical console. They are arranged, in some exemplary aspects, to securely hold the cassette in place with relatively little deviation from cassette to cassette. In embodiments disclosed, this may allow aspiration and irrigation pressure sensors to obtain precise pressure measurements during actuation of the fluidic pump and valves during cataract surgery.

In addition, the systems, devices, and methods, permit a surgeon or other health care provider to easily attach the cassette to the console and to easily remove the cassette. The systems are configured in at least some aspects to provide a relatively evenly distributed clamping force on the cassette from top to bottom and side to side, providing increased predictability and repeatability. In additional aspects, the system utilizes spring compensating moment arms to provide a more consistent clamping force over a larger range of clamping distances with reduced dependence on tight tolerances. As they displace, these spring compensating moment arms maintain a relatively effective moment force acting on the cassette by compensating for increases in spring force occurring as a result of spring extension.

Furthermore, components of the systems may be relatively easily removed and replaced as desired, permitting relatively easy assembly, removal, and repair. For example, the clamp mechanism utilizes a clamp bracket subassembly which assembles very easily to the module—pinch the top clamp levers, pull forward, and lift up. Removal is just as simple. Further, the clamp may be produced with relatively inexpensive fabrication methods utilizing, for example, sheet metal instead of machining. This results in lower manufacturing costs that can be passed on to the customer so that hospitals and clinics can more easily increase their capabilities and stock their surgical supplies. In addition, the arrangement of the clamp mechanism allows the clamp motor and other components to mount directly to a face plate. That is, in some aspects, the face plate can be machined from the front and back and does not require machining from the sides. That is, some aspects have no holes or taps on the side edges. In some aspects, the clamp facilitates use of a bezel which sheds fluid to the outside of the console. In addition, the bezel may utilize snapping tabs for ease of assembly or removal. This may help prevent water ingress. Further, in some aspects, the clamp mechanism has a relatively small footprint, allowing the width of the console to be more compact than in prior designs.

FIG. 1 illustrates an exemplary emulsification surgical console, generally designated 100. The console 100 includes a base housing 102 with a computer unit 103 and an associated display screen 104 showing data relating to system operation and performance during an emulsification surgical procedure. The console 100 also includes a number of systems that are used together to perform the emulsification surgical procedures. For example, the systems include a foot pedal system 106 including, for example, a foot pedal 108, a fluidics system 110 including a fluidics cassette 112 with a single flow control pump that both irrigates and aspirates the eye through flexible tubing 114, and an ultrasonic generator system including an ultrasonic oscillation handpiece 118 with a cutting needle. These systems overlap and cooperate to perform various aspects of a cataract surgical procedure.

Figure 2:
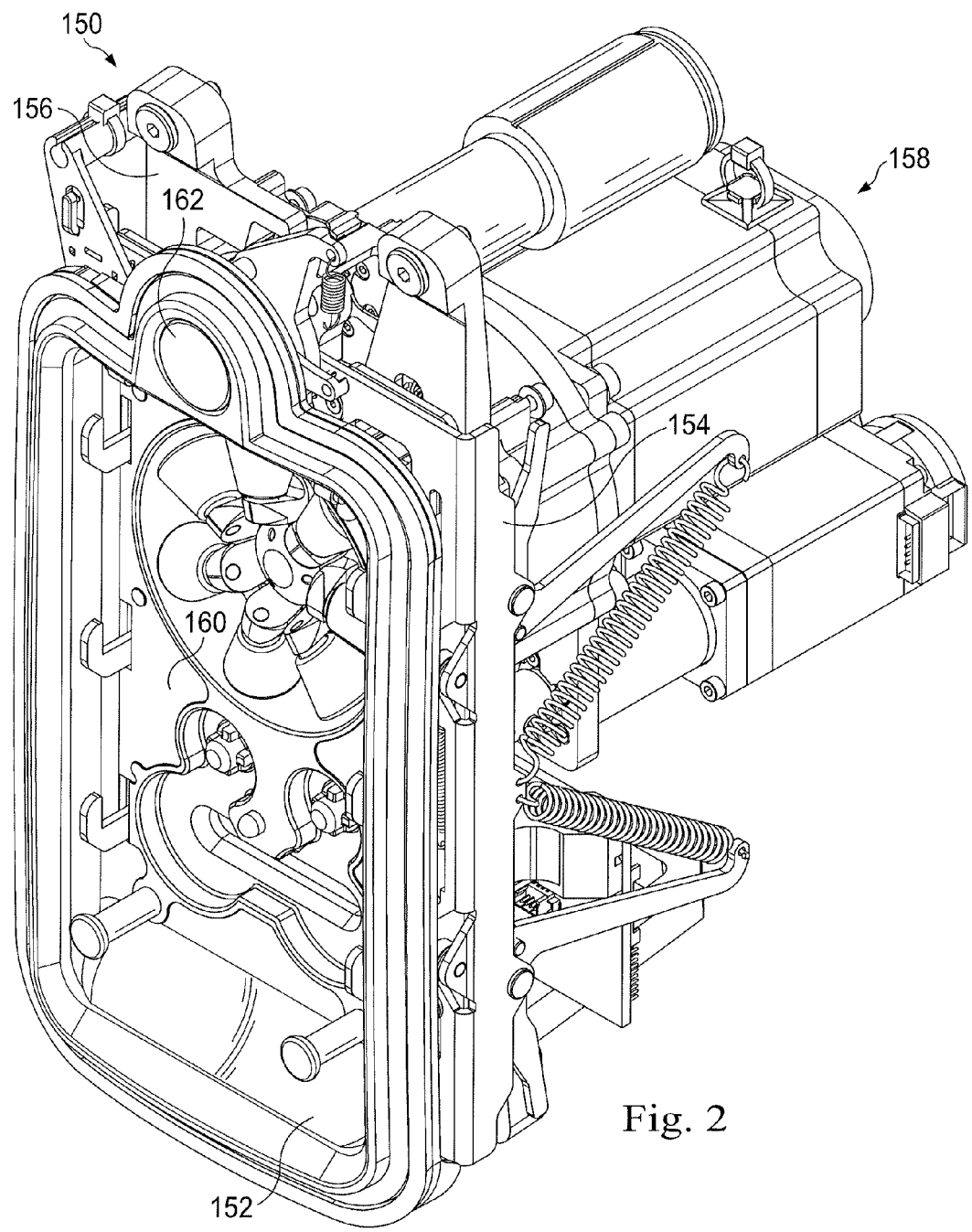
FIG. 2 is an illustration of an exemplary cassette clamp system according to an aspect consistent with the principles of the present disclosure.
Figure 3:
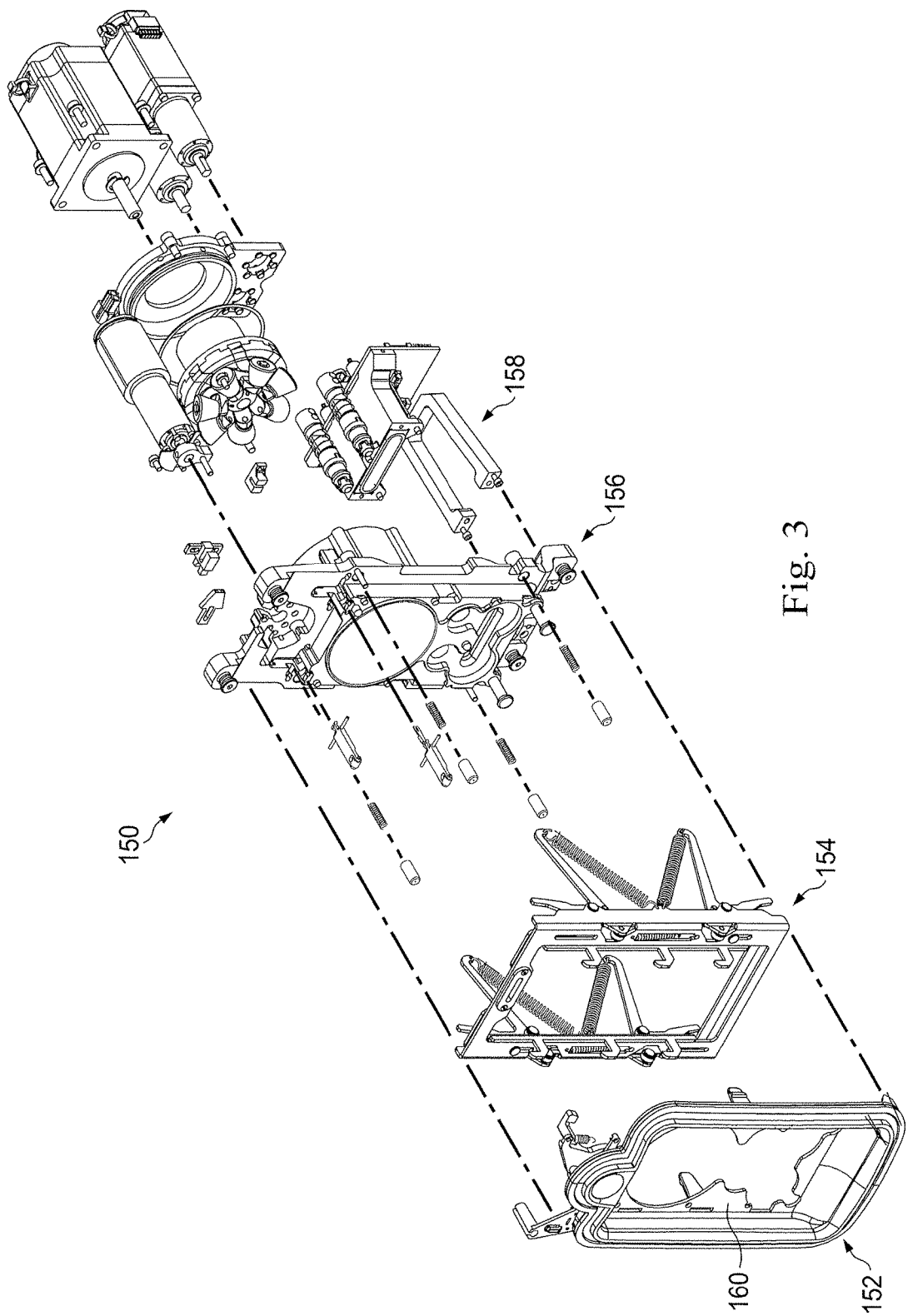
FIG. 3 is an illustration of an exemplary cassette clamp system in a partially exploded configuration according to an aspect consistent with the principles of the present disclosure.

FIG. 2 illustrates a cassette clamp system 150 forming a part of the fluidics system 110, and FIG. 3 shows the cassette clamp system 150 in a partially exploded condition. The cassette clamp system 150 is configured to receive and secure a fluid cassette used to carry irrigation fluids and aspiration fluids to or from the surgical site.

Referring to both FIGS. 2 and 3, the cassette clamp system 150 includes a plastic bezel 152, a clamp bracket assembly 154, a faceplate 156, and a motor and pump assembly 158.

The exemplary bezel 152 is, in this exemplary aspect, a plastic frame structure having a receiving portion 160 configured to receive the fluid cassette and configured to protect and cover the components behind it, such as the clamp bracket assembly 154. In this embodiment, the receiving portion 160 is rectangular shaped and includes a plurality of slots, openings, and cut-outs that provide access to portions of the clamp bracket assembly 154 and other components and elements of the cassette clamp system 150, while providing an aesthetic, clean appearance. Along a periphery of the receiving portion 160, the bezel 152 accommodates an ejection button 162 forming a part of a cassette release arrangement. This ejection button 162 is disposed at a location just above the receiving portion 160 and is located so that a user may press the button with a finger or thumb while catching or accessing the ejecting fluid cassette with other fingers of the same hand. Accordingly, the button 162 is disposed in a location that promotes and enables simple ejection and removal of a fluid cassette from the console 100. The bezel 152 may reduce fluid ingress into the console 100 and the cassette clamp system 150. It may shed fluid to the outside of the console 100. In one embodiment, the bezel 152 utilizes snapping tabs to connect to the console 100 for ease of assembly and removal. These snapping tabs, in some embodiments, are disposed along the peripheral edges and fit into mating receiving holes formed in the body of the console 100. Accordingly, the bezel may be introduced and snapped into the place as the tabs fit into the holes in the body of the console. Other connection features are also contemplated.

Figure 4:
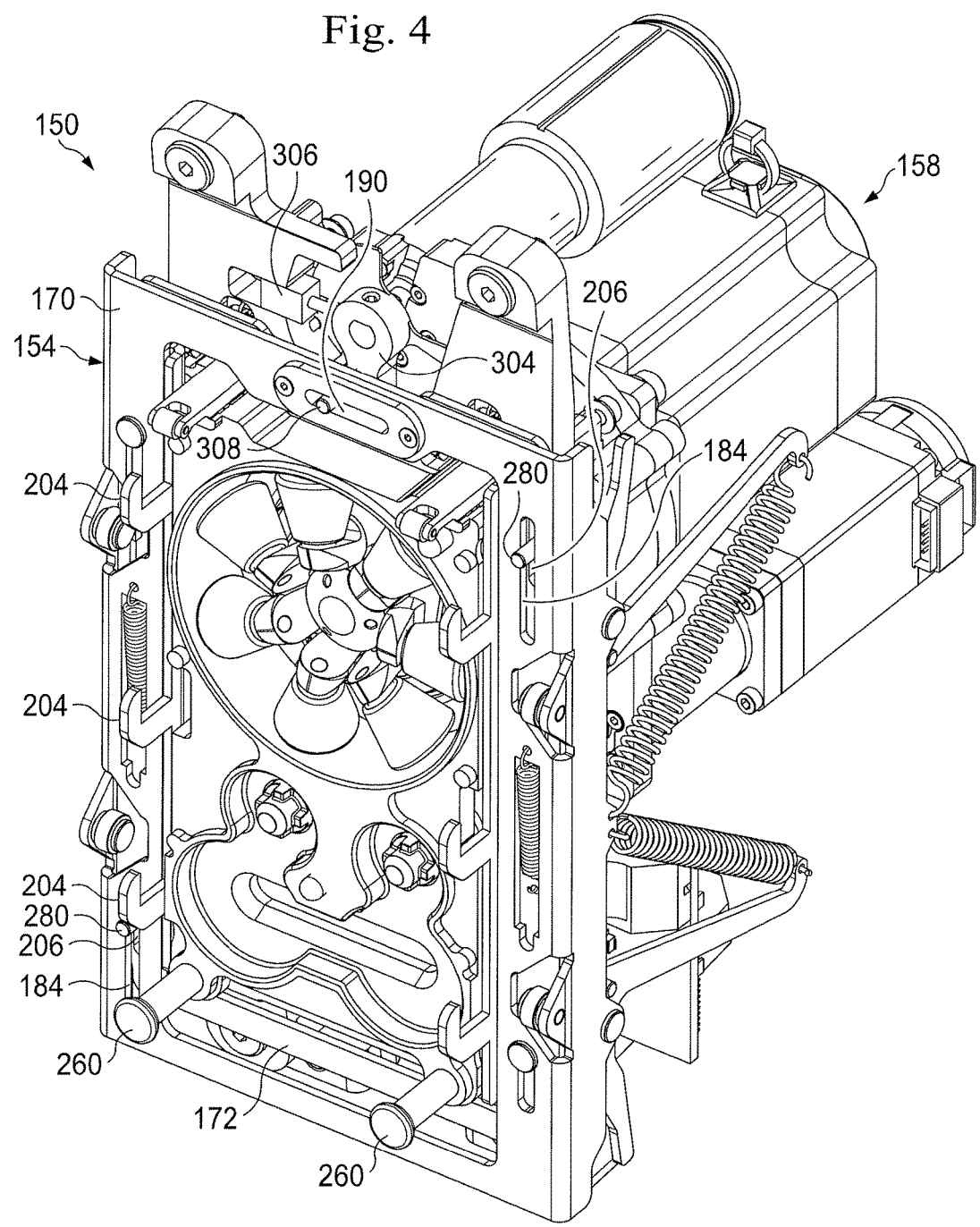
FIG. 4 is an illustration of an exemplary cassette clamp system with a bezel removed according to an aspect consistent with the principles of the present disclosure.
Figure 5:
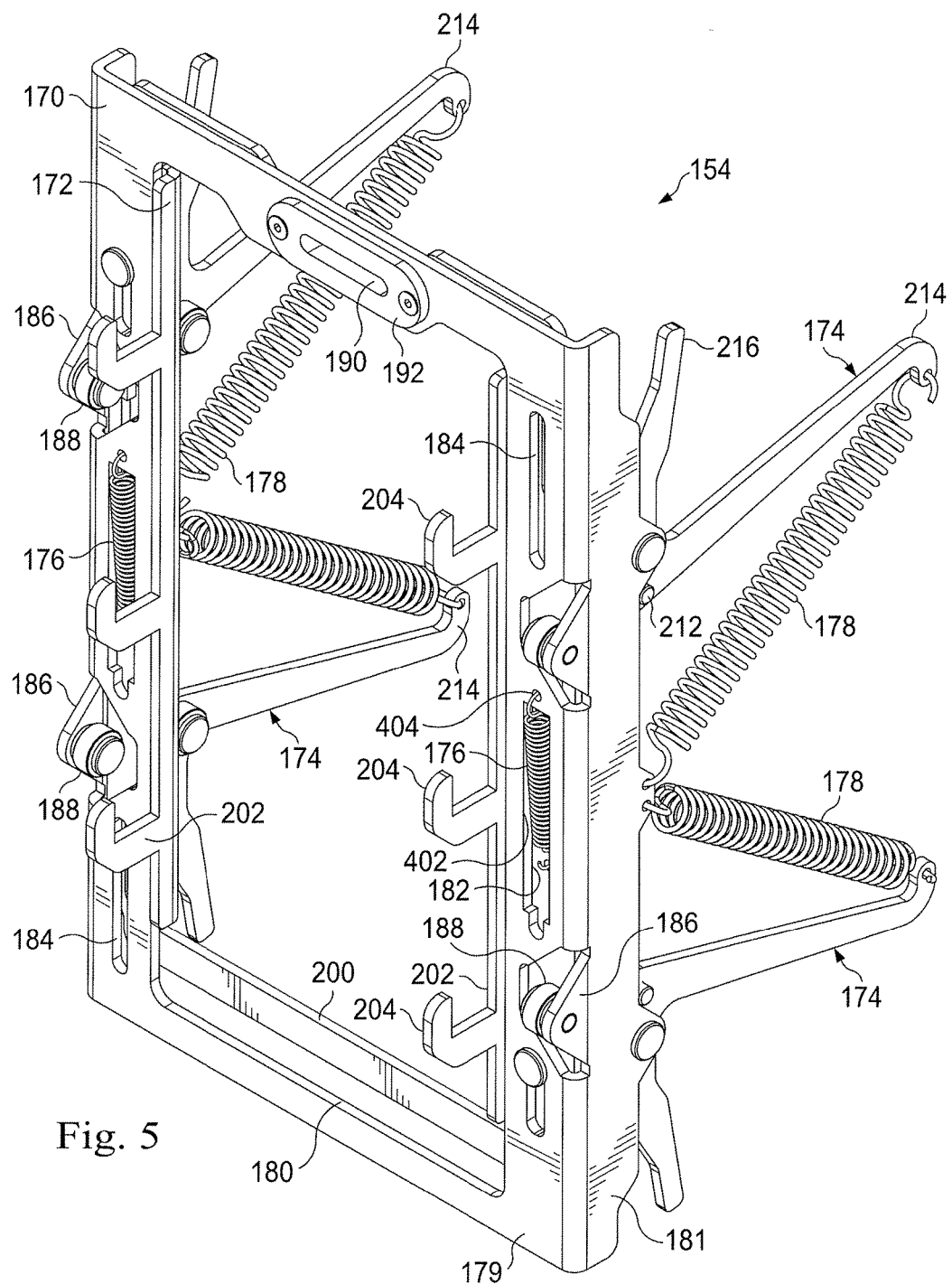
FIG. 5 is an illustration of an exemplary clamp bracket assembly of the cassette clamp system of FIG. 2 according to an aspect consistent with the principles of the present disclosure.
Figure 6:
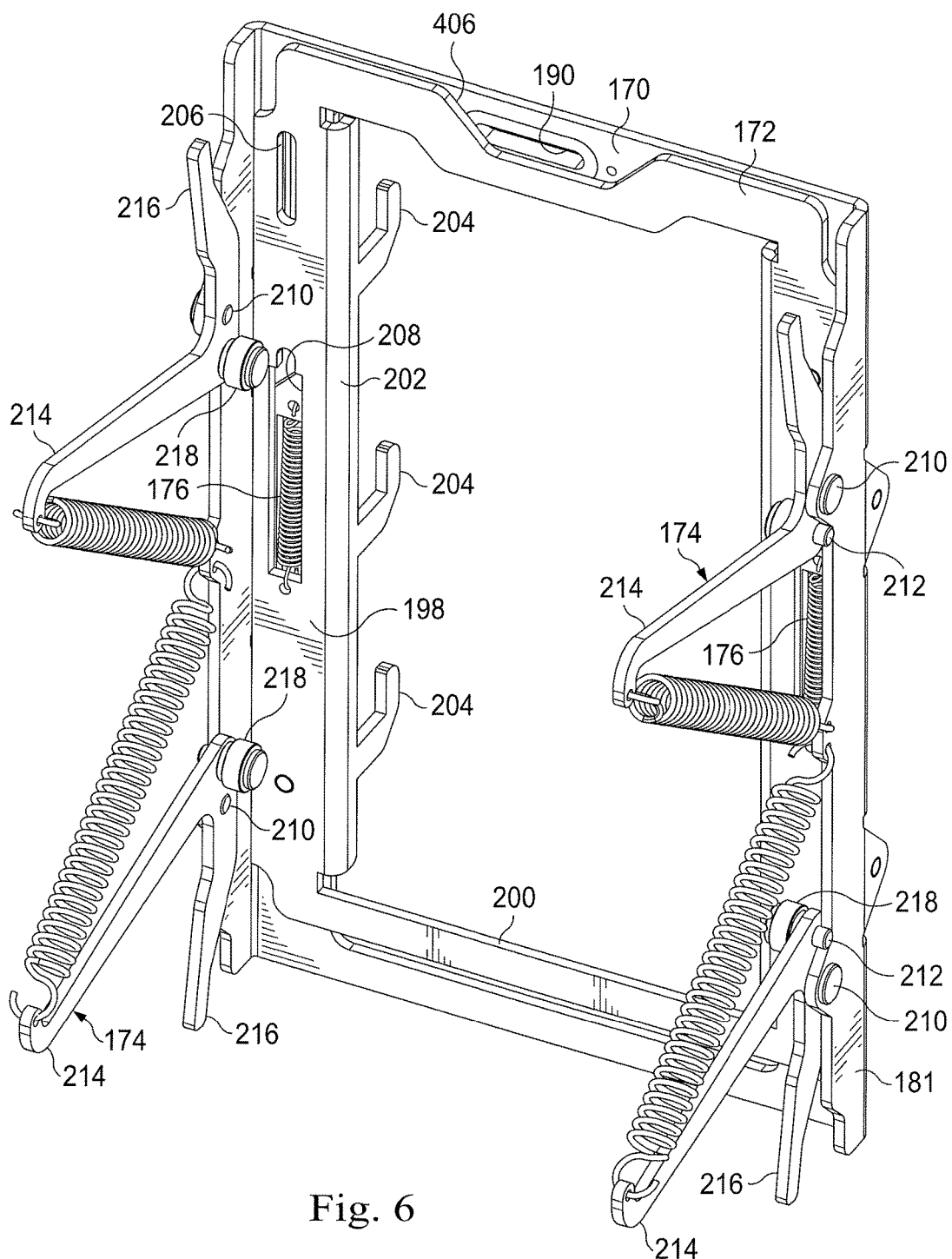
FIG. 6 is an illustration of another view of the exemplary clamp bracket assembly of FIG. 5 according to an aspect consistent with the principles of the present disclosure.
Figure 7:
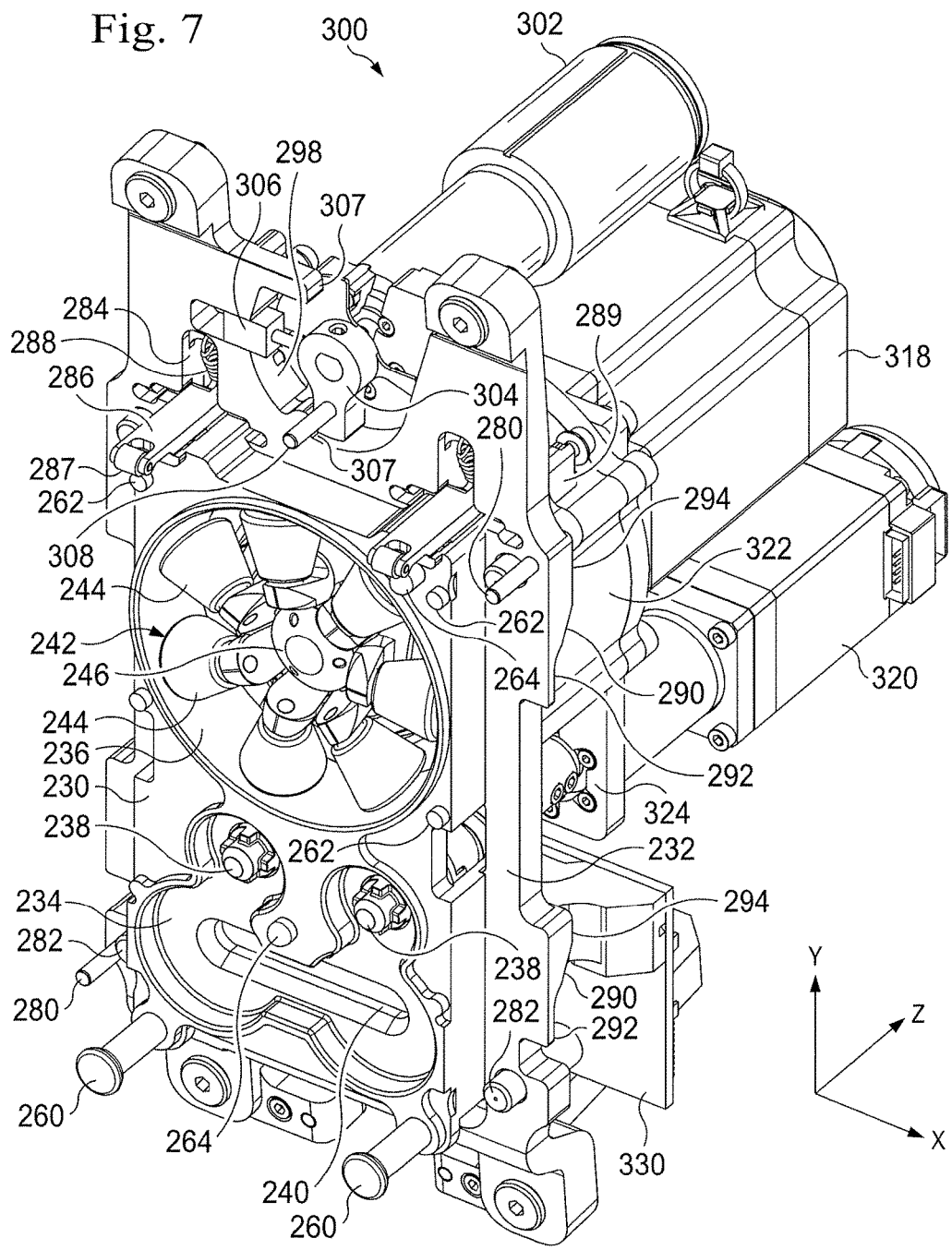
FIG. 7 is an illustration of an exemplary cassette clamp system having the bezel and the clamp bracket removed according to an aspect consistent with the principles of the present disclosure.

FIG. 4 shows the cassette clamp system 150 with the bezel removed and a view of the clamp bracket assembly 154 in place relative to the faceplate 156 and the motor and pump assembly 158. FIGS. 5-7 show the cassette clamp assembly 150 independent of other components of the cassette clamp system 150. The cassette clamp assembly 150 is configured to engage the fluid cassette, and draw it into its proper location for consistent, predictable operation.

Referring to FIGS. 4-7, the clamp bracket assembly 154 includes a motion bracket 170, a clamp bracket 172, a plurality of pivot arms 174, and a plurality of biasing elements, shown in this exemplary embodiment as clamping springs 176 and connector springs 178.

The motion bracket 170 is disposed adjacent the bezel 152 and acts as a connector to which other components of the clamp bracket assembly 154 connect. The motion bracket 170 includes a cutout central region 180 that provides access to other components of the cassette clamp system 150, including components of the faceplate 156 and the motor and pump assembly 158. The cutout central region 180 in this embodiment is rectangular shaped so that the motion bracket 170 forms a frame, through which the other components may be accessed and may operate.

The motion bracket 170 is formed of sheet metal and, therefore, is bent and cut to have particular features that enable smooth and proper operation. In this example, it includes a frame 179 and sides 181 with biasing member connections 182 formed of a slot 402 and connector hole 404 in the frame 179 through which the clamping springs 176 extend to connect the motion bracket 170 and the clamp bracket 172. It also includes a long guide pin slots 184 disposed at opposing corners that are used to limit the movement. This will be discussed further below.

Tabs 186 and rollers 188 carried on the tabs 186 provide a smooth relative movement along parallel planes of the motion bracket 170 and the clamp bracket 172. In this embodiment, the rollers 188 are secured to the motion bracket 170 and sized to engage the clamp bracket 172 through the cutouts formed by the tabs. These rollers 188 space the surface of the clamp bracket 172 away from the surface of the motion bracket 170 so that they do not have surface to surface contact as they move relative to each other.

In this exemplary embodiment, the motion bracket 170 includes a motion slot 190 that is disposed transverse to the direction of movement (in this example, the direction of movement is in the vertical direction). The motion slot 190 is configured to receive a motion pin that literally raises and lowers the motion bracket 170. A cut-out 406 in the clamp bracket (seen in FIG. 6) permits the pin (to be discussed below) to extend from the faceplate 156 to the motion bracket 170. In this example, an additional reinforcement element 192 provides a smooth and supporting surface for the interface with the motion pin.

The clamp bracket 172 is configured to be carried by the motion bracket 170, but also moves independently of the motion bracket 170. The clamp bracket 172, like the motion bracket 170 is formed of sheet metal. It comprises a flat plate forming a frame 198, with a central opening 200. Lateral sides 202 of the clamp bracket 172 are bent at 90-degree angles to project through the central cutout 180 of the motion bracket 170 in the direction of the bevel 152. These sides 202 include a plurality of fastening elements shown as tangs 204 formed therein that are sized and configured to engage and secure the fluid cassette. These tangs 204 extend out through the openings and cutouts in the bezel 152 to engage the fluid cassette. The fluid cassette likewise has features that correspond to and engage with the tangs 204.

Like the motion bracket 170, the clamp bracket 172 includes a guide pin slot 206 and a biasing member connection 208. The guide pin slot 206 aligns with the guide pin slot 184 of the motion bracket 170. The guide pin slot 206 however has a length smaller than that of the guide pin slot 184 so that when the clamp bracket assembly 154 moves relative to a guide pin in the guide pin slots 184, 206, the travel distance of the motion bracket 170 is greater than the travel distance of the clamp bracket 172. This occurs because the end of the short guide pin slot 206 engages and interferes with the guide pin, thereby providing a mechanical stop.

The biasing member connection 208 is formed as a cutout within the frame 198 and is aligned with the biasing member connection 182. In this example, it is sized to receive the clamping spring 176.

The clamping spring 176 is disposed within the biasing member connections 182, 208 and one end connects to the motion bracket 170 and the other end connects to the clamp bracket 172 in a manner that biases the clamp bracket 172 to a neutral position. This clamping spring 176 therefore, maintains the motion bracket 170 and the clamp bracket 172 in a position relative to each other so that the clamp bracket 172 moves with the motion bracket 170. However, when the clamp bracket 172 guide pin slot 206 engages the guide pin, the clamp bracket motion is prevented, while the motion bracket 170 may continue to move. This introduces tension into the clamping spring 176, and further movement is against the force of the clamping spring 176. It should be noted that other biasing arrangements are contemplated, including coil springs, elastomeric bumpers, leaf springs, and other types of springs and biasing systems.

The sides 181 of the motion bracket 170 include pivot connectors 210 that connect the pivot arms 174 to the motion bracket 170. The pivot arms 174 include a motion stop 212, a connector end 214, and a grab point 216. The motion stop 212 extends from a side of the pivot arm 174 and is disposed proximate the pivot connector 210. The motion stop 212 prevents over rotation of the pivot arm 174 by mechanically engaging an edge of the sides 181. The connector end 214 extends in a direction substantially opposite that of the tangs 204. These ends 214 are formed to connect with the connector springs 178. The grab point 216 extends from the pivot connector 210 and is used primarily during the assembly process.

In addition, the pivot arms 174 carry engagement portions as rollers 218 configured to engage with and travel along a portion of the faceplate 156 as will be described below. Connectors attach the motion bracket 170 to the clamp bracket 172 and prevent inadvertent disassembly of the clamp bracket assembly 154. The connectors extend through a slot in the motion bracket 170 and are fixed in place relative to the clamp bracket 172.

The connector springs 178 extend from the connector end 214 of the pivot arms 174 to the side 181 and bias the pivot arms to a position that will be described below.

FIG. 7 shows the cassette clamp system 150 with the bezel 152 and the clamp bracket assembly 154 removed. Accordingly, the faceplate 156 can be easily seen in FIG. 7. The faceplate 156 includes a number of connecting elements that help secure the fluid cassette in place on the console 100. The face plate 156 includes a relatively projecting central face 230, and a relatively recessed perimeter 232. The central face 230 is configured to project through the central openings 180, 200 in the motion bracket 170 and the clamp bracket 172.

The central face 230 includes a recessed portion configured to receive features of the fluid cassette, enabling the fluid cassette to engage features of the motor and pump assembly 158. For example, the central face 230 includes a valve drive recess 234 and a pump head recess or passage 236. The fluid cassette is shaped to have a projecting feature that projects into the valve drive recess 234. It can then engage and be driven by valve drives 238 that project from the motor and pump assembly 158. The valve drive recess 234 also includes an optical opening 240, shown here as a laterally extending opening. Through the optical opening 240, cameras, such as, for example, as optical pressure sensors, detect diaphragm movement on the fluid cassette to monitor pressures and/or flow through the fluid cassette. In addition, in some embodiments, the optical opening 240 is configured to use laser detection to determine when a fluid cassette is seated in the cassette clamp system 150. In the absence of a fluid cassette being detected through the optical opening 240, the motor and pump assembly 158 will not operate to pump even if such a command is provided by an input at the console 100.

As can be seen the pump head recess or passage 236 is configured to align and provide access to the pump head 242 of the motor and pump assembly 158. The pump head 242 is configured to engage against and drive fluid through the fluid cassette when the fluid cassette is engaged with the cassette clamp system 150. The pump head 242 includes a plurality of rollers 244 radially extending from a central hub 246.

The central face 230 also includes a plurality of projecting features configured to engage or align with the fluid cassette or the clamp bracket assembly 154. For example, the central face 230 includes an orientation element shown as shelf pins 260 used to orient a fluid cassette, landing pads 262 against which the fluid cassette may be pulled, and alignment pins 264 used to ensure the fluid cassette is properly positioned. The orientation element, the landing pads 262, and the alignment pins 264 project outwardly through receiving passages in the bezel 152 as shown in FIG. 2 to engage a fluid cassette. In this embodiment, the orientation element comprises two projecting shelf pins 260. These shelf pins 260 are spaced apart a distance to correspond with spaced receiving notches on the fluid cassette itself. While two shelf pins 260 are shown, any number of shelf pins may be used. Furthermore, the orientation element may be any number of alternative elements that may assist in orienting and aligning the fluid cassette.

The perimeter face 232 of the faceplate 156 is recessed relative to the central face 230 and disposed behind the clamp bracket assembly 154 when the cassette clamp system 150 is an assembled condition. The perimeter face 232 includes a plurality of features and projections that interface with the clamp bracket assembly 154 and the fluid cassette to secure the fluid cassette in place on the console 100. For example, the perimeter face 232 includes projecting guide pins 280 and spring cups 282 that extend outwardly from the perimeter face 232.

The projecting guide pins 280 are sized to extend into the guide pin slots 184, 206 on the motion bracket 170 and the clamp bracket 172. In this embodiment however, they do not extend through the bezel 152. In the exemplary embodiment shown, the spring cups 282 are distributed in the general area of the four corners of the face plate and push against the clamp bracket to bias the clamp bracket to an outward position.

The perimeter face 232 also includes a through slot 284 therein providing a passage to the motor and pump assembly 158. Retaining arms 286 pass through these slots 284 and are configured to engage a top perimeter of the fluid cassette to maintain the fluid cassette in place on the cassette clamp system 150.

The retaining arms 286 comprise a roller 287 at their distal end that is sized and configured to roll over an edge of the fluid cassette, pivotably displacing the retaining arms 286, until the roller seats within an indentation in the perimeter edge of the fluid cassette. Biasing members, shown as springs 288, bias the retaining arms 286 to the position shown, which is the neutral position and the clamped position.

Some embodiments include a sensor 289 associated with one or more retaining arms 286 that detects the position of the retaining arms 286 to identify whether a fluid cassette is present in the cassette clamp system 150. For example, some embodiments include an optical sensor that is configured to monitor a portion of the retaining arm 286 to detect when the arm 286 is displaced from its neutral position and to detect when the arm 286 is in a position that indicates it is seated in an edge of a fluid cassette. The sensor may communicate with a controller that sets a flag preventing operation of the cassette clamp system 150 until the sensor detects that a fluid cassette is present and properly seated. In one embodiment, the sensor detects the presence of a portion of the retaining arm 286 at a particular portion. While an optical sensor is used in some embodiments, other embodiments employ other types of sensors, including rotary sensors, piezoelectric sensors, or other transducers that can be used to detect positions and orientations to deduce the presence of the fluid cassette.

Opposite the perimeter face 232, the exemplary faceplate 156 includes a backside having tapered ramps 290 extending between a low region 292 (as defined by the thickness of the faceplate 156) to a high region 294. These ramps 290 cooperate with the rollers 218 on the pivot arms 174 on the motion bracket 170 so that as the clamp bracket assembly 154 displaces vertically (or in the y direction), the rollers 218 ride along the ramp 290, thereby causing the clamp bracket assembly 154 to simultaneously displace toward the perimeter face 232 and the motor and pump assembly 158 (the z direction). In some embodiments, the simultaneous directional displacement occurs only for the motion bracket 170, while the clamp bracket 172 moves in the y direction and is stopped by a guide pin prior to being pulled in the z direction as the motion bracket 170 continues to move. As it does this, the tangs 204 of the clamp bracket 172 pull the fluid cassette in the z direction, causing the fluid cassette to seat in the cassette clamp system 150.

Still referring to FIG. 7, the perimeter face 232 also includes a clamping cutout 298 that accommodates a clamping driving assembly 300. The clamping driving assembly 300 includes a clamp motor 302 forming a part of the motor and pump assembly 158, a drive wheel 304, and an optical sensor 306.

The drive wheel 304 is associated with a drive shaft of the clamp motor 302, either directly or indirectly, such as through a gear box. Accordingly, the clamp motor 302 may rotate the drive wheel 304 about a rotation axis. The drive wheel 304 includes a projecting drive pin 308 extending in a direction substantially parallel to the rotation axis; however, the projecting drive pin 308 is offset from the rotation axis. Accordingly, rotation of the drive wheel 304 by the drive motor 302 results in the drive pin 308 travelling in an arcing direction. In the embodiments shown, the drive wheel 304 travels from a position where the drive pin 308 is disposed directly below the rotation axis, or at a 6 o'clock position to a 12 o'clock position, where the drive pin 308 is disposed directly above the rotation axis. Other positions are also contemplated. In the embodiment shown, the drive wheel 304 engages motion limiting stops 307 that mechanically limit the rotation of the drive wheel 304. Accordingly, the drive wheel 304 may rotate between the stops 307 and may rotate until the stops 307 are engaged.

The drive pin 308 is sized and shaped to extend into the slot of motion slot 190 of the motion bracket 170 (FIG. 5). Accordingly, as the drive wheel 304 rotates and the drive pin 308 correspondingly travels in an arc, the vertical displacement (or the movement in the y direction) of the drive pin 308 results in a corresponding vertical displacement of the clamp bracket assembly 154. The length of the motion slot 190 in the transverse or x-direction permits lateral travel within the slot 190 so that the while drive pin 308 travels in an arc, the clamp bracket assembly 154 moves only in the vertical direction, along the y-direction.

The optical sensor 306 is disposed adjacent the drive wheel 304 and is configured to detect the position of the drive wheel 304. Accordingly, it may be used to sense when the drive wheel 304 is in a fully locked position, indicating that the fluid cassette is secured in the console and detect when the drive wheel 304 is in a fully unlocked position. Other types of position sensors are also contemplated, including displacement sensors, encoders, and others.

The motor and pump assembly 158 includes the clamp motor 302, a pump motor 318, a valve drive motor 320 and a pump 322 connected by a motor mounting plate 324. In some embodiments, the motor and pump assembly 158 also includes the optical pressure sensors detecting pressures through the optical opening 240 and a controller shown as a PCB (Printed Circuit Board) 330 fixed to the optical pressure sensors.

In operation, a user, such as a health care provider, can attach a fluid cassette to the console by introducing the fluid cassette to the cassette clamp system 150. To do this, the user may rest the fluid cassette on the orientation element formed of the shelf pins 260. The fluid cassette body itself may have a perimeter shaped to accommodate the orientation element. With one edge (e.g., the bottom edge) of the fluid cassette resting on the orientation element, the opposing edge (e.g., the upper edge) may be pivoted toward the retaining arms 286. The retaining arms 286 are disposed so that the rollers 287 mechanically interfere with the opposing edge (e.g., upper edge) of the fluid cassette as it is introduced into the cassette clamp system 150. As the fluid cassette advances, the rollers 287 displace and roll over the leading edge of the fluid cassette causing the retaining arms 286 to pivot as they accommodate the displacement. This displacement is against the biasing force of springs 288. Accordingly, when the rollers 287 reach the seats formed in the edge of the fluid cassette, the rollers snap into place in the seats, and the retaining arms 286 retain the fluid cassette in place on the cassette clamp system. In some embodiments, the rollers 287 may extend and snap onto the face of the cassette instead of snap into seats in the cassette periphery. In yet other embodiments, instead of rollers, the retaining arms 286 include fastening elements as hooks or other fasteners.

As explained above, a sensor 289 may be used to track displacement or the location of one or more of the retaining arms 286 as a check to confirm when the retaining arm 286 is properly located, indicating that the retaining arm is correctly engaged with the fluid cassette and that the fluid cassette is properly positioned. In this example, the sensor may be an optical sensor, although other types of sensors also may be used.

Likewise, a sensor disposed behind the optical opening 240 may also detect whether the fluid cassette is properly positioned. This sensor may be a proximity sensor that detects when an object, such as the fluid cassette is disposed in front of the optical opening 240. This sensor could be any of a plurality of different types of sensors. Furthermore, this sensor may be arranged in any of a number of other arrangements to detect when a fluid cassette is being positioned within the cassette clamp system 150. Furthermore, although the two sensors disclosed herein provide a level of redundancy, other embodiments use only a single sensor, while other embodiments use additional sensors.

The sensors communicate with a controller (shown as PCB 330) on the console 100 that operates to control a part of or the complete fluidics system 110. When the controller receives signals from the sensors that the fluid cassette is in place, the controller may control the clamp motor 302 to secure the fluids module in place.

In some embodiments, the controller may operate under its own initiative when the sensors detect the presence of the fluid cassette, while in other embodiments, the user must initiate the clamping process using an input control, such as pressing a button, turning a dial, operating the foot pedal, or otherwise inputting a command.

The clamp motor 302 operates by rotating the drive wheel 304 to move the drive pin 308 from a first position corresponding to an unclamped position to a second position corresponding to a clamped position. The unclamped position in this embodiment is when the drive pin 308 is relatively vertically lower than the clamped position, which in this embodiment is when the drive pin 308 is relatively higher. Since the drive pin 308 extends into the motion slot 190 in the motion bracket 170, a change in elevation of the drive pin 308 results in a corresponding change in elevation of the motion bracket 170. Since the motion bracket 170 is constrained against side-to-side or transverse movement in the x-direction, the motion bracket 170 can only move in the up or down direction as a result of the drive pin movement.

As described above, the clamp bracket 172 is biasedly connected to the motion bracket 170 by the clamping springs 176. Therefore, as the motion bracket 170 moves in the y-direction, so does the clamp bracket 172. That is, they move together.

Referring to FIG. 4, the guide pins 280 extend through the guide pin slot 184 in the motion bracket 170 and the guide pin slot 206 in the clamp bracket 172. These guide pins 280 constrain the movement of the clamp bracket assembly 154 and prevent lateral movement in the x-direction. For a short distance, the motion bracket 170 and the clamp bracket 172 move upwardly together as carried by the drive pin 308. During this upward movement, the tangs 204 of the clamp bracket 172 hook or otherwise move to a position that mechanically prevents removal of the fluid cassette. After the short movement in the y-direction, the bottom end of the guide pin slots 206 of the clamp bracket 172 contact the guide pins 280, and the guide pins 280 prevent further upward movement of the clamp bracket 172. However, since the guide pin slots 184 on the motion bracket 170 are longer than the guide pin slots 206 on the clamp bracket 172, the motion bracket 170 may continue to move in the y-direction. Since the motion bracket 170 continues to move upward, but the clamp bracket 172 is prevented from moving upward, the biasing force of the clamping spring 176 is overcome and the clamping spring 176 is further extended.

During the period of time discussed above where both the motion bracket 170 and the clamp bracket 172 move in the y-direction together, the rollers 218 on the pivot arms 174 are disposed substantially on the low region 292 on the backside of the faceplate 156 (FIG. 7). As the motion bracket 170 moves in the y-direction however, the rollers 218 roll up the ramp 290. As this occurs, the entire clamp bracket assembly 154 moves in the z-direction, pulling the tangs 204 against the fluid cassette and pulling the fluid cassette in the z-direction until it engages or abuts against the landing pads 262. It's worth noting that as the clamp bracket assembly 154 moves in the z-direction, it is acting against the biasing force of the spring cups 282, which bias the clamp bracket assembly 154 away from the perimeter face 232 of the faceplate 156. In some embodiments, the motion bracket 170 may move upward until the rollers 218 reach the high region 294 on the backside of the faceplate 156. In other embodiments, the y-axis travel of the motion bracket 170 stops with the rollers 218 on the ramp 290 before they reach the high region 294. Accordingly, when securing the fluid cassette, the tangs 204 may first move upward and then move inward.

When the fluid cassette abuts against the landing pads 262, the fluid cassette cannot move further in the z-direction. As such, the clamping bracket 172 and the motion bracket 170 cannot move further in the z-direction. However, because the rollers 218 are disposed on pivot arms, the rollers 218 may continue to roll up the ramp 290 as the pivot arms 174 pivot against the force of the connector springs 178. That is, while the motion bracket 170 cannot move in the z-direction, the rollers 218 may move in the z-direction by forcing the pivot arms 174 to pivot about the pivot connectors 210. This occurs since the rollers 218 are offset from the pivot connectors 210. As the pivot arms 174 rotate however, the connector springs 178 are stretched further, increasing the clamping load or holding force on the clamp bracket 172 and the fluid cassette.

The sensor 306 may detect whether the drive wheel 304 is in a position indicative of a fully clamped condition. Accordingly, until the drive wheel 304 is fully rotated to a clamped position, the controller may not permit further use of the fluidics module. However, if the sensor 306 communicates with the controller that the drive wheel 304 is in a position indicating that the fluid cassette is fully clamped, and the sensors at the optical opening 240 and at the retaining arm 286 indicate that the fluid cassette is properly seated, then the controller may permit further operation of the fluidics system 110. With the fluid cassette secured in the cassette clamp system 150, the fluidics system 110 can monitor flow through the fluid cassette using the optical sensors, and flow may be controlled using the foot pedal, another input device, or simply through control programming.

The cassette clamp system 150 is set up to operate in reverse to permit removal of the fluid cassette. In this embodiment, pressing the ejection button 162 activates the controller to run the clamp motor 302 in the opposite direction, rotating the drive wheel 304 from the clamped position to the unclamped position, and displacing the clamp bracket assembly 154 in the manner described above to loosen and permit removal of the fluid cassette.

Some embodiments of the present disclosure are arranged to provide a relatively consistent clamping force on the fluid cassette despite differences in fluid cassette thickness. That is, even though the clamp bracket 172 may displace in the z-direction a distance that varies from fluid cassette to fluid cassette, the clamping force remains substantially the same. This occurs because the clamp bracket assembly 150 employs a variable moment arm. This consistency in clamping force results in increased consistency in cassette position and cassette operation.

Fluid cassettes that have differing thickness can result in the fluid cassette engaging or abutting against the landing pads 262 at when the clamp bracket 172 is at different positions in the z-direction. As such, the clamp bracket 172 with its tangs 204 may travel in the z-direction a greater distance with one fluid cassette than with another fluid cassette. In some of the embodiments described above, this variation in travel in the z-direction results in variation in the degree of pivoting by the pivot arm 174. In this embodiment, the connector springs 178 connect to the motion bracket 170 and the end of the pivot arms 174 at locations that result in a relatively consistent clamping force despite differences in displacement in the z-direction. It does this because the length of the moment arm (distance of a line segment perpendicular to the connector spring 178 and through the pivot point defined by the pivot connector 210) decreases as the spring 178 lengthens. Therefore, as the spring force increases by virtue of the extending spring 178, the length of the moment arm correspondingly decreases. In this example, the spring 178 and the connection locations of the spring 178 on the motion bracket 170 and on the pivot arm 174 are selected so that the clamping force is relatively consistent even when the amount of rotation of the pivot arm 174 changes.

Figure 8:
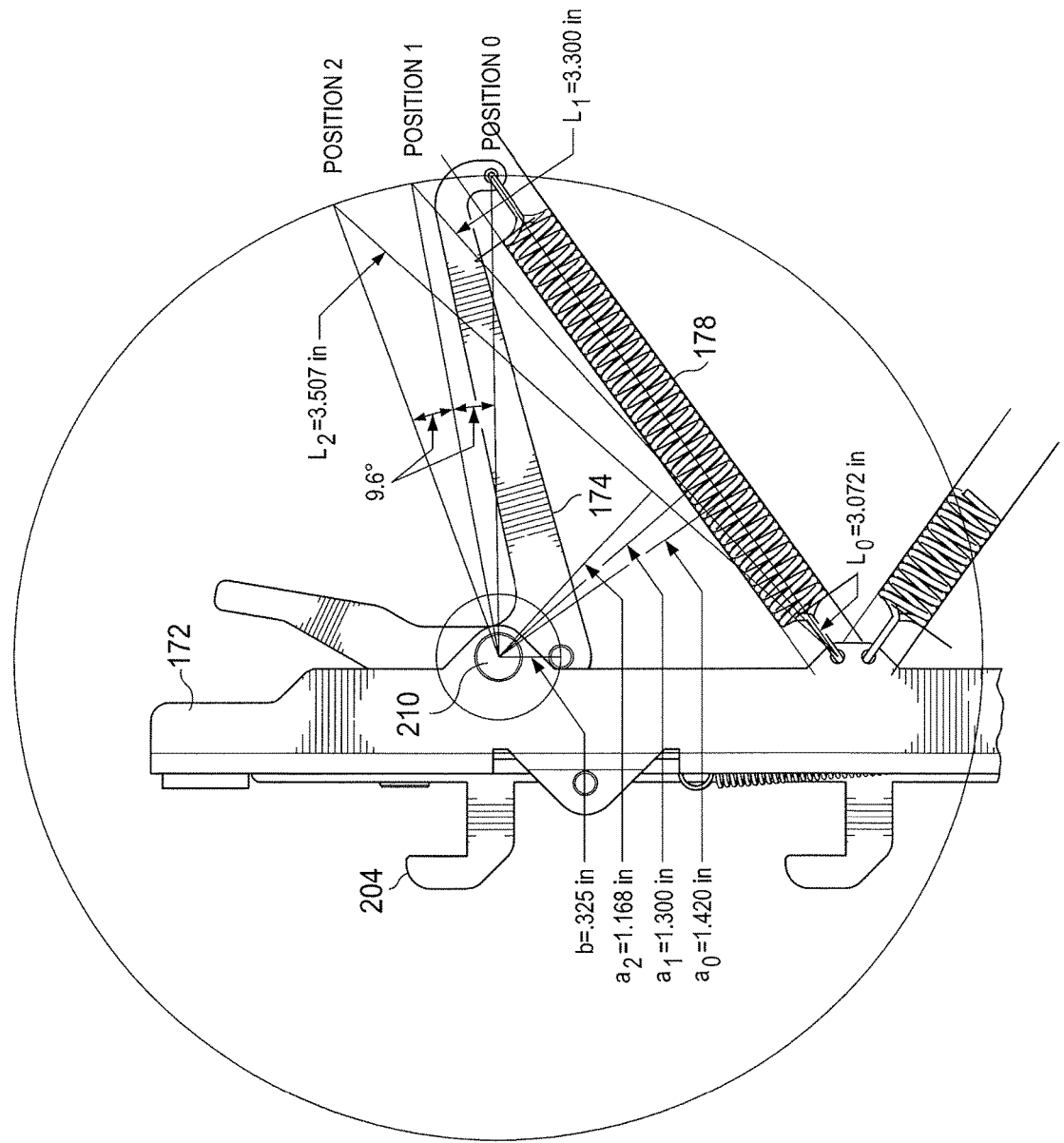
FIG. 8 is an illustration of an exemplary clamping arrangement with a variable moment arm according to an aspect consistent with the principles of the present disclosure.

The operation of this is shown in FIG. 8 in the context of the clamp bracket 172, the pivot arms 174, and the spring 178. Accordingly, in the example in FIG. 8, the spring 178 is selected with a spring constant of about 2.9 lb/in. (pounds/inch), a free spring length of about 2.0 in, and an initial tension of 0.60 lb. The mechanism geometry provides mechanical advantage of about 4 to 1 for spring to clamping force with clamping moment arm of about 0.325 in and variable moment arm for the spring of about 1.30 in at position 1. For an arm rotation of about 9.6 degrees between positions 0 and 1, and another 9.6 degrees between positions 1 and 2, the mechanism geometry establishes the variable moment arm length to be about 1.42 in at position 0, 1.30 in at position 1, and 1.18 in at position 2, corresponding to a stretched spring length of about 3.07 in at position 0, 3.30 in at position 1, and 3.51 in at position 2, so that the resulting clamping force per arm at is about 16.2 lb at position 0, 17.48 lb at position 1, and 17.87 lb at position 2. This is a change of only 2.23% between position 1 and 2. This is an improvement over a system that uses a near constant moment arm of 1.30 in, as the resulting force would change by about 14.1%, from 17.48 lb to 20.00 lb per arm between position 1 and 2. The effect of the variable moment arm in this example is to reduce the effective spring constant by a factor of 6.4 from 2.9 lb/in to about 0.45 lb/in between positions 1 and 2. In this example, the difference between position 1 and position 2 is the equivalent of the cassette thickness variance of about 0.054 in.

In another similar example, the spring 178 is selected with a spring constant of about 3.10 lb/in, a free spring length of about 1.88 in, and an initial tension of about 1.00 lb. Using the same mechanical geometry as the above example, the resulting clamping forces per arm are 20.51 lb at position 0, 21.61 lb at position 1, and 21.75 at position 2, a change of only 6.05% for an equivalent cassette thickness variance of about 0.104 in from position 0 to position 2. Or a change of only 0.65% from position 1 to position 2 which is an equivalent cassette thickness variance of about 0.054 in. The effect of the variable moment arm in this example is to reduce the effective spring constant by a factor of 19.2 from 3.1 lb/in to about 0.161 lb/in from position 1 to position 2.

As used herein, a relatively consistent clamping force is intended to include clamping force variations of less than about 10% when thicknesses differ by about 0.05 in. In some embodiments, it includes clamping force variations of less than about 5%, while in other embodiments it includes clamping force variations of less than about 3% when thicknesses differ by about 0.05 in.

Figure 9:
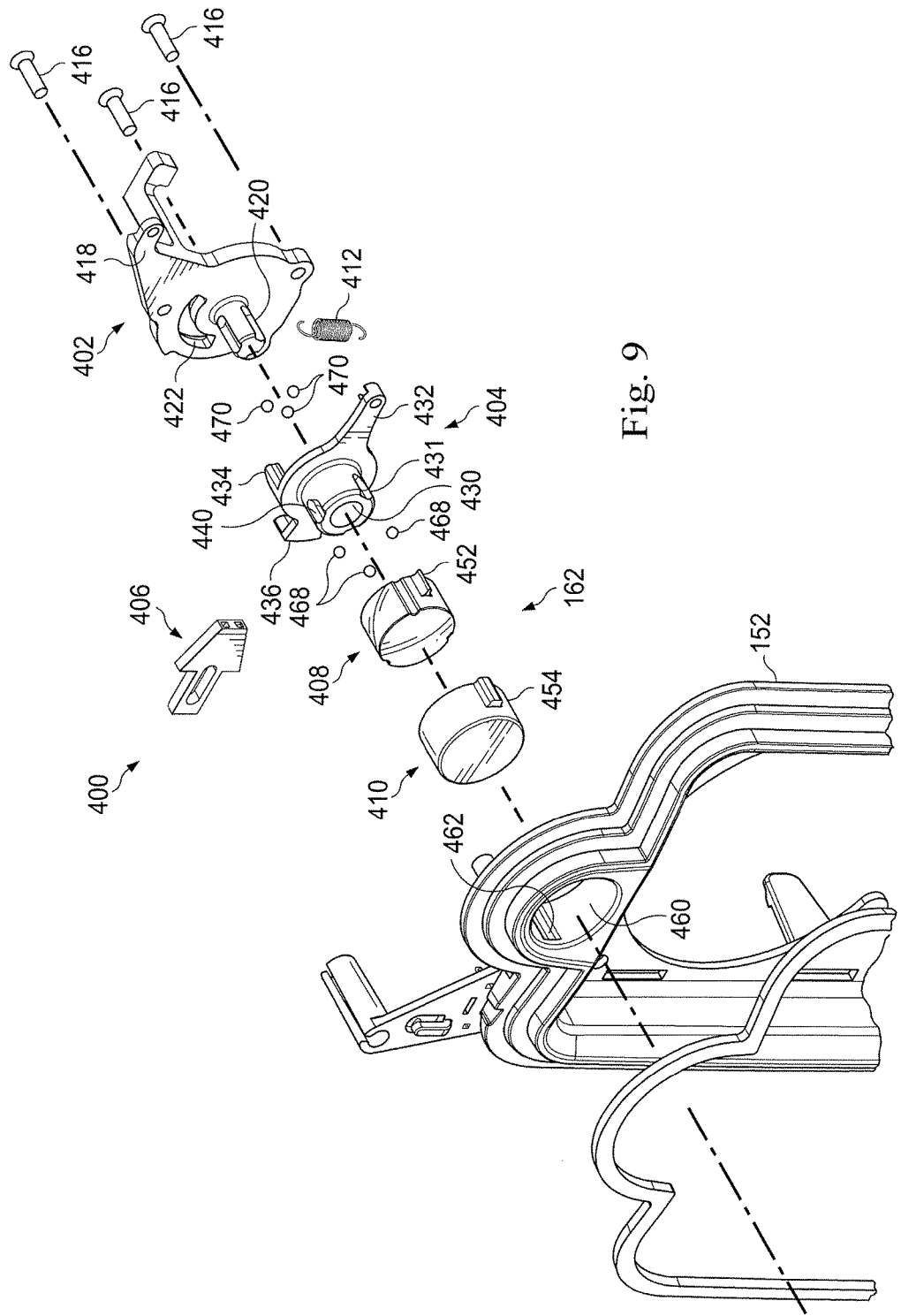
FIG. 9 is an illustration of an exemplary cassette release arrangement in an exploded view according to an aspect consistent with the principles of the present disclosure.
Figure 10:
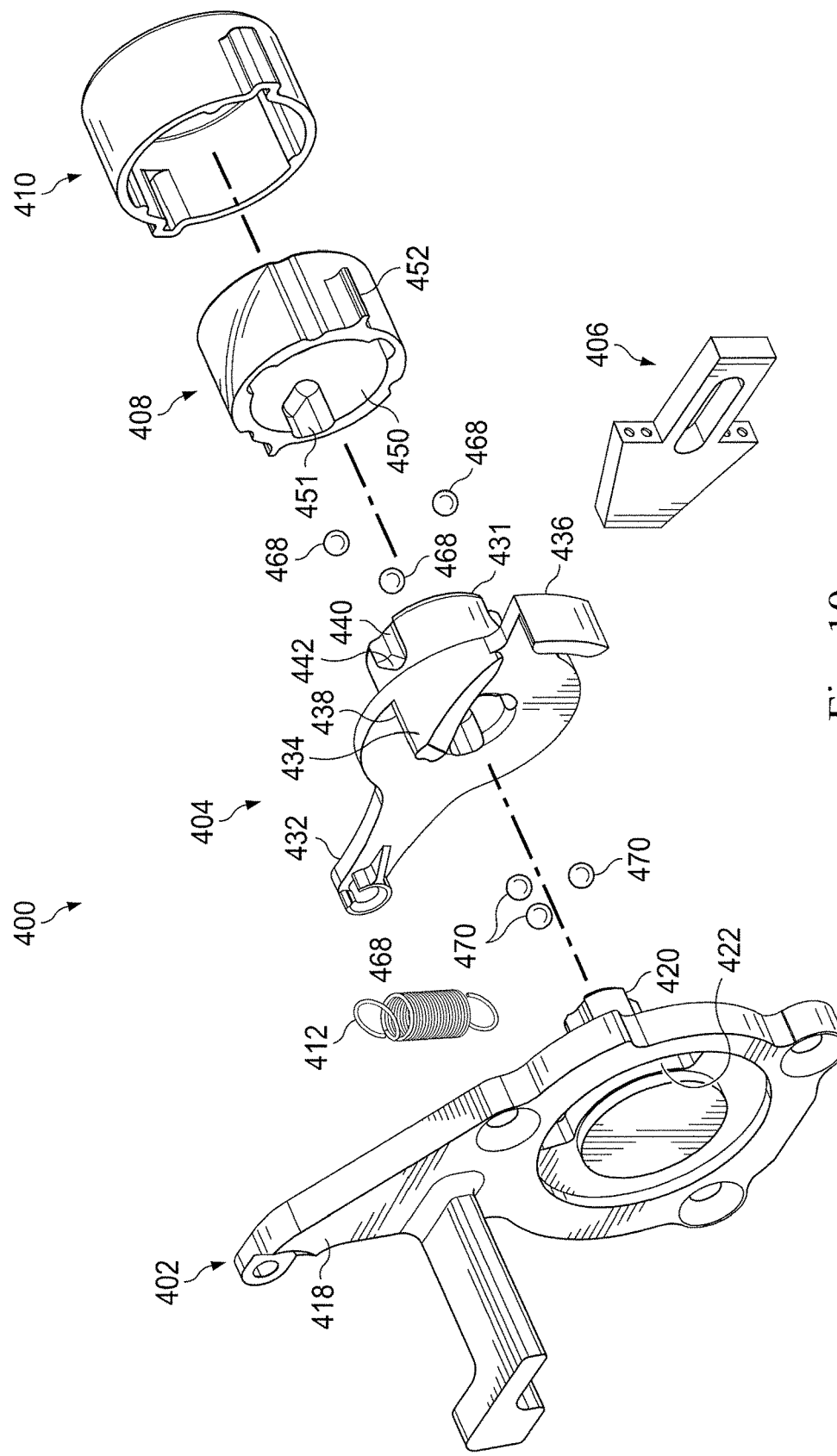
FIG. 10 is an illustration of the exemplary cassette release arrangement of FIG. 9 from another angle according to an aspect consistent with the principles of the present disclosure.
Figure 11:
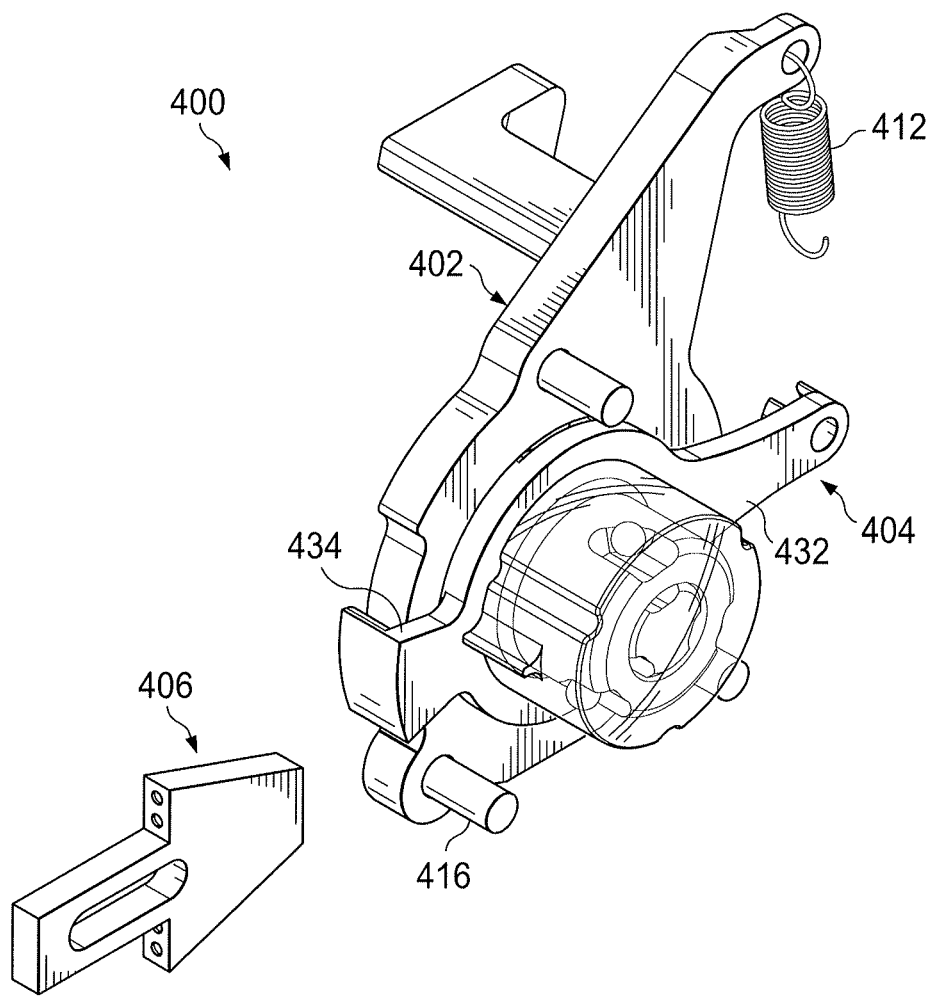
FIG. 11 is an illustration of the exemplary cassette release arrangement of FIG. 9 according to an aspect consistent with the principles of the present disclosure.

FIGS. 9-11 show details of a cassette release arrangement 400 that may be employed to release the cassette or initiate a release of the cassette from the console.

In this embodiment, the cassette release arrangement 400 permits a user to (a) release the cassette using a powered approach where the clamp motor 302 (FIG. 7) rotates the drive wheel 304 (FIG. 7) from the clamped position to the unclamped position to release and permit removal of the fluid cassette, and also permits a user to (b) mechanically release the cassette without the use of power to operate the clamp motor. As such, even after the system is off or unplugged, a fluidics cassette may still be manually ejected in order to prepare the system for use in a subsequent surgery. Therefore, the user need not reboot or power the system for the sole purpose of removing the fluid cassette.

In the exemplary embodiment shown in FIGS. 9-11, the cassette release arrangement 400 connects to the bezel 152 and includes a support portion 402, a rotating insert 404, a sensor 406 such as an optical sensor, and the button 162 including a button body 408 and a button cover 410. In the assembled condition shown in FIG. 11, a biasing element 412 extends between and connects the support portion 402 and the rotating insert 404, and biases the rotating insert 404 to a secured position.

The support portion 402 connects via fasteners, such as screws 416, to the bezel 152. It includes an extension spring arm 418, a central knob 420, and a clearance slot 422 that receives a part of the rotating insert 404. Since it connects to the bezel 152, the support portion 402 is substantially fixed in place, and the various components of the cassette release arrangement move relative to the support portion 402.

The rotating insert 404 includes a central bore 430 extending through a boss 431, an extension spring arm 432, a finger portion 434, and a flag portion 436. The central bore 430 receives the central knob 420 and the rotating insert 404 pivots about the central knob 420. The finger portion 434 protrudes through the clearance slot 422. As shown in FIG. 10, the finger portion 434 includes a driving surface 438 that is configured to engage the drive pin 308 extending into the motion slot 190 of the motion bracket 170 (FIG. 5). The flag portion 436 is arranged to be disposed adjacent the sensor 406.

The boss 431 is a cylindrical portion having a plurality of rotational channels 440 formed therein. In this embodiment, the rotational channels 440 are helical channels or are slots having a bottom shaped as a helical surface 442. These help convert axial motion to rotary motion as described below.

The sensor 406 is disposed adjacent the flag portion 436 and is configured to detect the position of the rotating insert. The sensor 406 communicates with the controller (shown as PCB 330 in FIG. 7) on the console 100. When the controller receives signals from the sensor 406 that the flag portion 436 is in a particular position, the controller may control the clamp motor 302 to rotate to release a clamped fluids cassette. In one embodiment, the sensor 406 is an optical sensor and the flag portion 436 includes a flag surface having an anodized portion and a reflective portion. In one example, when the anodized portion is adjacent the sensor 406, the sensor 406 does not send a signal however, when the reflective portion of the flag portion 436 is adjacent the sensor 406, the sensor 406 may send a signal to controller, and the controller may operate the clamp motor 302 to release the fluid cassette.

The button body 408 includes a hollow portion 450 that receives the boss 431 of the rotating insert 404. The button body 408 also includes rotational channels 451 on an inner surface of the hollow portion 450 and includes wings 452 projecting from its outer surface. The button cover 410 may provide electrical isolation. In this embodiment, it is disposed over the button body 408 and includes matching wings 454.

The button cover 410 and button 408 fit within a bore 460 on the bezel 152. The wings 454 fit within slots 462 in the bore 460 and prevent rotation of the button body 408 and the button cover 410.

Ball bearings 468 are disposed within the rotational channels 442, 451, which together form a helical travel path for the ball bearings 468. In this embodiment, additional ball bearings 470 disposed between the rotating insert 404 and the support portion 402 provide smooth relative rotation between the two components.

In use, the cassette release arrangement 400 converts linear motion to rotational motion via a helical interface formed by the rotational channels 440, 451. The sensor 406 detects the rotational motion of the flag portion 436 so that the control circuit can initiate the mechanism to release a cassette. If the system is powered down, the rotational motion of the rotating insert 404 brings the driving surface 438 on the finger portion 434 into contact with the projecting drive pin 308 (FIG. 7) on the drive wheel 304 (FIG. 7) and pushes it so that it rotates "over center" and the clamp releases from the mechanical energy stored in the clamping springs. The button 162 is restrained to move only in the Z direction. The rotating insert 404 is restrained to only rotate about Z axis. The biasing element 412 (e.g., a spring) extends between and connects the extension spring arm 418 and the extension spring arm 432 and returns the rotating insert 404 back to its starting position when the button 162 is released, which in turn biases the button 162 back to the starting position. While shown in a disconnected form in FIG. 11, the spring 412 extends into and connects the extension spring arm 418 and the extension spring arm 432. This also pushes both sets of ball bearings back to their starting positions—this assures that they will have sufficient travel to provide for rolling.

When the button is pushed, the rotating insert 404 rotates until the sensor 406 detects the rotation, and the controller then operates the clamping motor to release the cassette. However, in the absence of power, further pushing of the button 162 moves the rotating insert 404 further, causing the driving surface 438 on the finger portion 434 to push the projecting drive pin 308 from its position over-center. This also may cause the rollers 218 to move to a position on the ramps 290, permitting the pent-up potential energy in the system via the springs to cause the clamp bracket assembly to displace and release the cassette.

As further discussed above, in some embodiments, a method for interfacing a surgical cassette to a surgical console may include (a) receiving a surgical cassette on an orientation element configured to orient the surgical cassette for clamping in a surgical console, (b) detecting the presence of the surgical cassette with a first sensor, (c) engaging the surgical cassette with a plurality of fastening elements disposed at adjacent corners of the surgical cassette to evenly distribute a clamping force and move the fastening elements in a first direction, and (d) fixing the surgical cassette in place by moving the fastening elements in a second direction. In some embodiments, receiving a surgical cassette on an orientation element may include receiving the surgical cassette on a plurality of projecting shelf pins shaped to correspond to features of the surgical cassette. In some embodiments, engaging the surgical cassette may further include engaging the surgical cassette with six fastening elements with a substantially equal clamping force on each fastening element. In some embodiments, fixing the surgical cassette in place by moving the fastening elements in a second direction may include driving a bracket system along a ramp. In some embodiments, the method may further include maintaining the surgical cassette on the console with a plurality of retaining arms that engage a perimeter of the surgical cassette.

The methods and systems described herein provide a consistent clamping position and consistent clamping force, while maintaining simplicity and elegance in design. While the terms up, down, and lateral are used herein, these terms are merely intended to be used as examples based on the embodiment shown. It is equally understood that the coordinate frame could be changed to provide different modes of operation.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

We claim:

1. A surgical cassette clamping system comprising:
a bracket system comprising a fastening element configured to engage a surgical cassette;
a pivot arm pivotably connected to the bracket system at a pivot location; and
a clamp motor operably connected to the bracket system to move the bracket system in a first direction;
a biasing system between the pivot arm and the bracket system, the biasing system connecting to the bracket system at a first connecting location and connecting to the pivot arm at a second connecting location to maintain a relatively consistent clamping force on the fastening element engaging the surgical cassette;
wherein the bracket system is configured to move in the first direction, and the fastening element of the bracket system is configured to move in a second direction to secure the surgical cassette;
wherein the bracket system comprises a motion bracket and a clamp bracket, the clamp bracket comprising the fastening element and the motion bracket comprising the first connecting location.

2. The surgical cassette clamping system of claim 1, wherein as the bracket system is moved in the first direction, the fastening element of the bracket system is configured to simultaneously move in the second direction to secure the surgical cassette.

3. The surgical cassette clamping system of claim 1, wherein the relatively consistent clamping force is a clamping force that deviates less than about 10% over a pivot range of about 10 degrees.

4. The surgical cassette clamping system of claim 1, further comprising a clamping spring connecting the clamp bracket and the motion bracket.

5. The surgical cassette clamping system of claim 1, comprising rollers enabling smooth translation of the motion bracket relative to the clamp bracket.

6. The surgical cassette clamping system of claim 1, comprising a cassette release arrangement configured to convert linear motion into rotational motion to mechanically release the surgical cassette from the surgical cassette clamping system.

7. The surgical cassette clamping system of claim 6, wherein the cassette release arrangement comprises a controller and a position detector in communication with the controller, the controller being configured to electronically control release of the surgical cassette from the surgical cassette clamping system.

8. The surgical cassette clamping system of claim 1, further comprising:
a faceplate having a first side and a second side on an opposing side of the faceplate;

wherein the bracket system is disposed adjacent the first side of the faceplate, the bracket system comprising at least two connectors.

9. The surgical cassette clamping system of claim 1, wherein the biasing system is a spring.

10. The surgical cassette clamping system of claim 1, wherein the first direction is perpendicular to the second direction.

11. A surgical cassette clamping system comprising:
a bracket system comprising a fastening element configured to engage a surgical cassette;
a pivot arm pivotably connected to the bracket system at a pivot location; and
a clamp motor operably connected to the bracket system to move the bracket system in a first direction;
a biasing system between the pivot arm and the bracket system, the biasing system connecting to the bracket system at a first connecting location and connecting to the pivot arm at a second connecting location to maintain a relatively consistent clamping force on the fastening element engaging the surgical cassette;
wherein the bracket system is configured to move in the first direction, and the fastening element of the bracket system is configured to move in a second direction to secure the surgical cassette;
wherein the pivot arm comprises a roller spaced from the pivot location.

12. The surgical cassette clamping system of claim 11, further comprising a ramp disposed relative to the roller, the ramp displacing the bracket system in a direction to clamp the surgical cassette with the fastening elements, the ramp forcing the pivot arm to pivot about the pivot location as the bracket system moves.

13. The surgical cassette clamping system of claim 11, wherein as the bracket system is moved in the first direction, the fastening element of the bracket system is configured to simultaneously move in the second direction to secure the surgical cassette.

14. The surgical cassette clamping system of claim 11, wherein the relatively consistent clamping force is a clamping force that deviates less than about 10% over a pivot range of about 10 degrees.

15. The surgical cassette clamping system of claim 11, wherein the first direction is perpendicular to the second direction.

16. A surgical cassette clamping system comprising:
a bracket system comprising a fastening element configured to engage a surgical cassette;
a pivot arm pivotably connected to the bracket system at a pivot location; and
a clamp motor operably connected to the bracket system to move the bracket system in a first direction;
a biasing system between the pivot arm and the bracket system, the biasing system connecting to the bracket system at a first connecting location and connecting to the pivot arm at a second connecting location to maintain a relatively consistent clamping force on the fastening element engaging the surgical cassette;
wherein the bracket system is configured to move in the first direction, and the fastening element of the bracket system is configured to move in a second direction to secure the surgical cassette;
wherein the surgical cassette clamping system further comprises a faceplate having a first side and a second side on an opposing side of the faceplate;
wherein the bracket system is disposed adjacent the first side of the faceplate, the bracket system comprising at least two connectors;
wherein the clamp motor is disposed adjacent the faceplate and fixed relative to the faceplate; and
wherein the pivot arm is one of a plurality of pivot arms pivotably connected to the bracket system via the at least two connectors and extending adjacent the second side of the faceplate, wherein the plurality of pivot arms comprise rollers.

17. The surgical cassette clamping system of claim 16, wherein the second side of the faceplate comprises ramps;
wherein as the bracket system moves in the first direction relative to the faceplate, the rollers ride along the ramps such that the bracket system simultaneously moves in the second direction toward the first side of the faceplate.

18. The surgical cassette clamping system of claim 16, wherein as the bracket system is moved in the first direction, the fastening element of the bracket system is configured to simultaneously move in the second direction to secure the surgical cassette.

19. The surgical cassette clamping system of claim 16, wherein the relatively consistent clamping force is a clamping force that deviates less than about 10% over a pivot range of about 10 degrees.

20. The surgical cassette clamping system of claim 16, wherein the first direction is perpendicular to the second direction.

* * * * *